(12) United States Patent
Lomakin et al.

(10) Patent No.: US 10,729,802 B2
(45) Date of Patent: Aug. 4, 2020

(54) LIGHT-CURABLE FIXATION COMPOSITES AND SYSTEMS FOR ORTHOPEDIC STABILIZATION

(71) Applicant: Reboot Medical Inc., Lowell, MA (US)

(72) Inventors: Joseph Lomakin, Arlington, MA (US);
Madalyn Berns, Cambridge, MA (US);
Jeff Maynard, Allston, MA (US)

(73) Assignee: REBOOT MEDICAL INC., Lowell, MA (US)

( * ) Notice: Subject to any disclaimer, the term of this patent is extended or adjusted under 35 U.S.C. 154(b) by 448 days.

(21) Appl. No.: 15/808,574

(22) Filed: Nov. 9, 2017

(65) Prior Publication Data

US 2018/0126029 A1  May 10, 2018

Related U.S. Application Data

(60) Provisional application No. 62/419,929, filed on Nov. 9, 2016.

(51) Int. Cl.
*A61L 15/12* (2006.01)
*A61F 5/05* (2006.01)
(Continued)

(52) U.S. Cl.
CPC .............. *A61L 15/12* (2013.01); *A61F 5/05* (2013.01); *A61L 15/08* (2013.01); *A61L 15/14* (2013.01); *C08F 2/50* (2013.01); *C08K 7/14* (2013.01)

(58) Field of Classification Search
CPC .......... A61L 15/12; A61L 15/08; A61L 15/14; A61L 15/07; A61L 15/00; A61L 15/125; A61L 15/16; A61L 15/18; A61L 15/20; A61L 15/22; A61F 5/05; A61F 5/0102; A61F 5/04; A61F 5/01; A61F 5/00;
(Continued)

(56) References Cited

U.S. PATENT DOCUMENTS 3,881,473 A * 5/1975 Corvi ................. A61F 13/04
602/8
4,052,282 A * 10/1977 Kubushiro ............ A61L 15/12
602/8

(Continued)

OTHER PUBLICATIONS

International Search Report and Written Opinion of the International Searching Authority for Application No. PCT/US2017/060903 dated Feb. 19, 2018.

*Primary Examiner* — Tarla R Patel
(74) *Attorney, Agent, or Firm* — Foley & Lardner LLP

(57) ABSTRACT

The present technology relates to composites, apparatuses, systems, and methods that are based on a photocurable composite useful for stabilizing, supporting, or otherwise healing an injured limb. The photocurable composite includes a light-curable resin and a filler material, where the light-curable resin includes about 50 vol % to about 99 vol % (based on the volume of the light-curable resin) of an acrylate-functionalized oligomer, wherein the backbone of the oligomer comprises a polyurethane, a polyether, a polyester, or a combination of any two or more thereof; about 1 vol % to about 50 vol % of a radical-reactive diluent; about 0.001 vol % to about 2 vol % of a photoinitiator; and optionally about 0.05 to about 25 vol % of a surface cure protection agent.

19 Claims, 8 Drawing Sheets

(51) Int. Cl.
  *A61L 15/08* (2006.01)
  *A61L 15/14* (2006.01)
  *C08F 2/50* (2006.01)
  *C08K 7/14* (2006.01)

(58) Field of Classification Search
  CPC ... A61F 13/04; C08F 2/50; C08K 7/14; A61B 17/60
  USPC .............................................................. 602/8
  See application file for complete search history.

(56) References Cited

U.S. PATENT DOCUMENTS

| | | | |
|---|---|---|---|
| 4,330,590 A * | 5/1982 | Vesley | C08F 2/50 428/336 |
| 4,512,340 A | 4/1985 | Buck | |
| 6,100,206 A * | 8/2000 | Scholz | A61L 15/12 428/332 |
| 2009/0264551 A1* | 10/2009 | Nakasugi | A61F 5/05825 522/36 |
| 2014/0114001 A1* | 4/2014 | Choi | C08L 69/00 524/127 |

\* cited by examiner

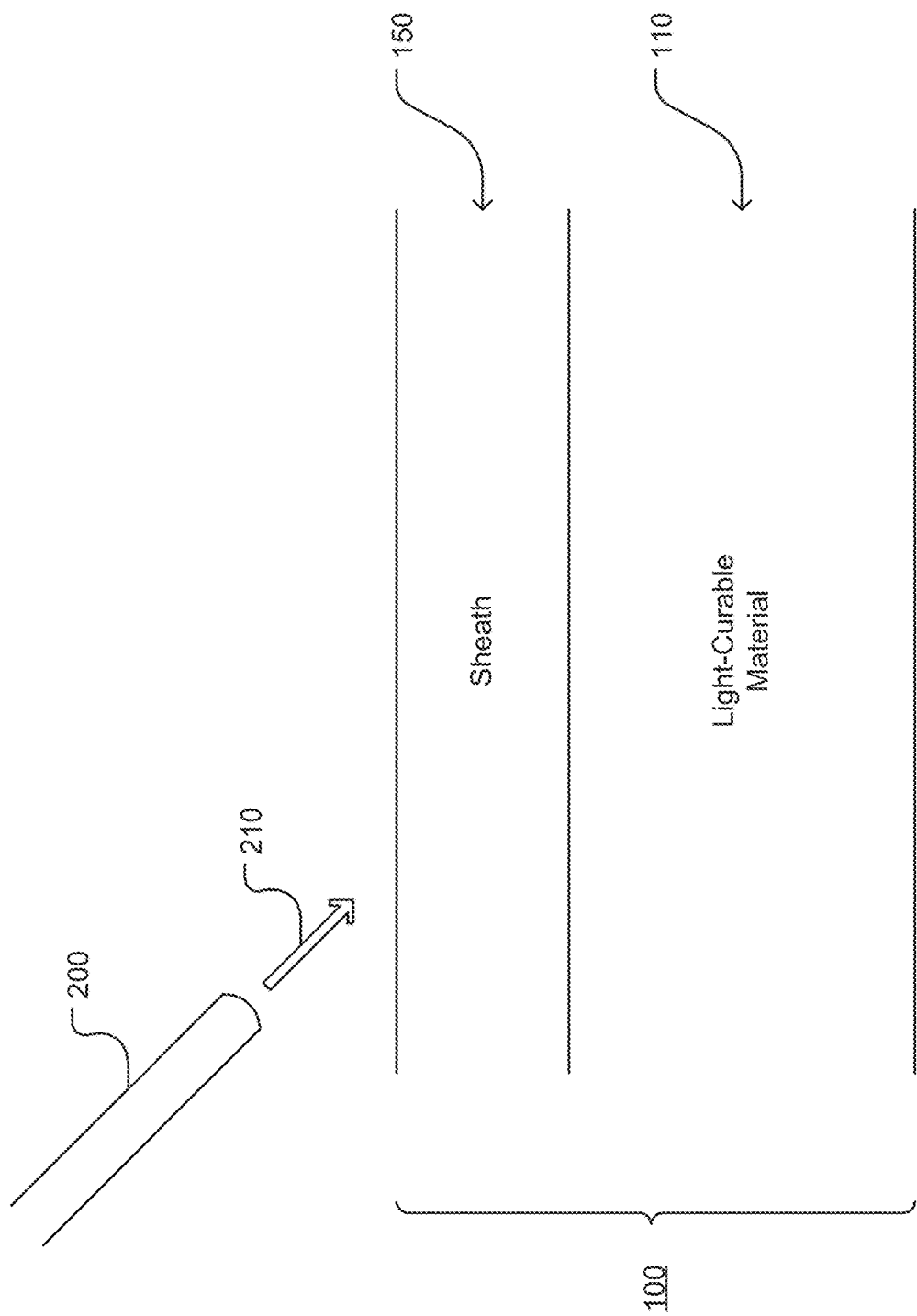

LIGHT-CURABLE FIXATION COMPOSITES AND SYSTEMS FOR ORTHOPEDIC STABILIZATION

CROSS-REFERENCE TO RELATED APPLICATIONS

This application claims priority to U.S. Provisional Appl. No. 62/419,929, filed Nov. 9, 2016, the contents of which are incorporated herein by reference for any and all purposes.

TECHNICAL FIELD

The present disclosure generally relates to systems and methods for treating injuries and supporting and stabilizing body portions using splints and medical casts.

BACKGROUND

A variety of splints and medical casts are available for orthopedic purposes, to treat injuries and support and stabilize body portions. Current solutions include casts and splints made of plaster, fiberglass, and thermoplastic. Plaster and fiberglass solutions provide high quality fixation but require ample drying time (plaster may require over 48 hours to become weight bearing) and have a set working life and therefore require high skill to apply. Additionally, water baths and exposure to hazardous chemistry result in messy applications often requiring extra protection (ex. fiberglass must be applied with gloves). Thermoplastic casts and splints are becoming more popular for less severe fractures but are not as stiff as traditional options and still require water baths or ovens that add additional prep and procedure time. Additionally, in hospital fracture care treatments (splints and casts) rely on plaster of Paris (PoP), fiberglass, and thermoplastics, materials. While these products may achieve adequate fixation, significant time (both during and after the procedure) is wasted waiting for material to achieve its final hardened form (fiberglass may require +30 min and plaster may require +48 hours to become weight bearing). Importantly, fiberglass and plaster rely on water baths for activation. The need for water contributes to risk of infection, increases mess during application, produces difficult to handle waste, and results in extra cleanup time.

SUMMARY

The present disclosure relates to composites, apparatuses, systems, and methods that are based on a photocurable composite useful for stabilizing, supporting, or otherwise healing an injured limb. The photocurable composite may improve over existing solutions, such as orthopedic and emergency casts and splints, by reducing the time to achieve full cure from half an hour or more to minutes, and making the device more adaptable to real-life applications. In some embodiments, the photocurable composite includes preform fiberglass or another composite filler, which may be pre-impregnated with a light-curable resin. When illuminated by a light source, the resin may polymerize and harden, causing the photocurable composite to transition to a hardened cast state (e.g., a functional cast). In a conformation or configuration of the photocurable composite, sections of the photocurable composite may be selectively cured, such that a first one or more sections may be cured at a first time while a second one or more sections may be cured at a second time. In another conformation or configuration of the photocurable composite, all of the light-curable resin of the photocurable composite is configured to be cured together (e.g., in response to a single activation trigger or the same activation trigger, such as a light-based trigger).

BRIEF DESCRIPTION OF THE FIGURES

FIG. 1 illustrates a schematic diagram of a system including a light-curable device, according to an embodiment of the present disclosure.

DETAILED DESCRIPTION

Figure 2A:
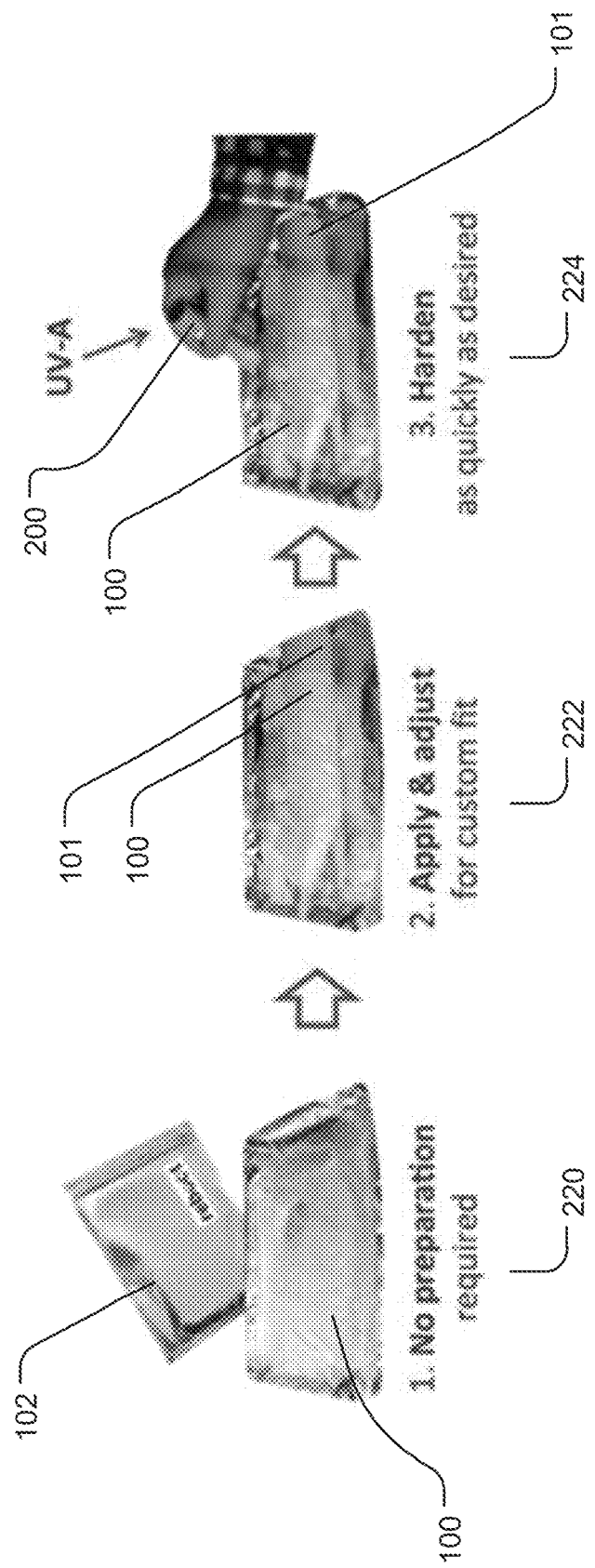
FIGS. 2A-2B illustrates flow diagrams of methods of using a system including a light-curable device, according to embodiments of the present disclosure.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, $C_m\text{-}C_n$, such as $C_1\text{-}C_{12}$, $C_1\text{-}C_8$, or $C_1\text{-}C_6$ when used before a group refers to that group containing m to n carbon atoms.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

As used herein, the term "repeat unit" refers to a structurally repeating unit of a polymer. A repeat unit may be a monomeric unit or an oligomeric unit (i.e., includes two or more monomeric units).

As used herein, the term "branch repeat unit" refers to a repeat unit that has a valence of three or more and is covalently attached to, or capable of covalently attaching to, three or more repeat units. Thus, for example, a styrene repeat unit in a polystyrene polymer does not constitute a branch repeat unit.

As used herein, the term "backbone" refers to a longest chain of a polymer.

As used herein, the term "oligomer" refers to a structure that contains a relatively small number of monomeric units. As used herein, the term includes any structure having two or more monomeric units.

As used herein, the term "polymer" refers to a molecule that contains one or more monomer units.

As used herein, a "subject" or "patient" is a mammal, such as a cat, dog, rodent or primate. Typically the subject is a human, and, preferably, a human suffering from or suspected of suffering from pain. The term "subject" and "patient" can be used interchangeably.

The term "acrylate-functionalized" as used herein is well understood by a person of ordinary skill in the art and will vary to some extent depending upon the context in which it is used. If there are uses of the term which are not clear to persons of ordinary skill in the art, given the context in which it is used, "acrylate-functionalized" will mean the compound has at least one

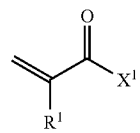

where $X^1$ is independently at each occurrence an oxygen, nitrogen, or sulfur atom of the compound that is "acrylate-functionalized," and $R^1$ is independently at each occurrence H, alkyl, or CN.

The phrase "substantially free" as used herein means less than about 0.1 wt. %, preferably less than about 0.01 wt. %.

The terms "visible range", "visible light," and "visible light spectrum" as used herein refers to the portion of the electromagnetic spectrum that is visible to the typical human eye and will be understood by persons of ordinary skill in the art. If there are uses of the term(s) which are not clear to persons of ordinary skill in the art, given the context in which it is used, the term(s) means electromagnetic radiation in the range from about 380 nm to about 700 nm. The term "UV light" refers to electromagnetic radiation in the range from about 100 nm to about 400 nm, where "UV-A" refers to electromagnetic radiation in the range from about 315 nm to about 400 nm and "UV-B" refers to electromagnetic radiation in the range from about 280 nm to 315 nm.

A variety of splints and medical casts are available for orthopedic purposes, to treat injuries and support and stabilize body portions. Current solutions include casts and splints made of plaster, fiberglass, and thermoplastic. Plaster and fiberglass solutions provide high quality fixation but require ample drying time (plaster may require over 48 hours to become weight bearing) and have a set working life and therefore require high skill to apply. Additionally, water baths and exposure to hazardous chemistry result in messy applications often requiring extra protection (ex. fiberglass must be applied with gloves). Thermoplastic casts and splints are becoming more popular for less severe fractures but are not as stiff as traditional options and still require water baths or ovens that add additional prep and procedure time. Existing devices would be improved by reducing prep, application, cleanup, and cure times. Quick procedures aid doctors with busy schedules, increase patient throughput, and free up limited hospital resources. Patients would benefit from less expensive procedures and are inconvenienced by long dry or cure times.

The present technology provides a reinforcement system which may include an activation device, and a photocurable composite configured to transition from a soft state to a hardened state in response to an activation trigger received from the activation device, including a light-based activation trigger. The activation device may be configured to generate, transmit, and/or output light selected to cause a desired activation.

In an aspect, a photocurable composite is provided which includes a light-curable resin and a filler material. The light-curable resin includes about 50 vol % to about 99 vol % (based on the volume of the light-curable resin) of an acrylate-functionalized oligomer, wherein the backbone of the oligomer comprises a polyurethane, a polyether, a polyester, or a combination of any two or more thereof; about 1 vol % to about 50 vol % of a radical-reactive diluent; about 0.001 vol % to about 2 vol % of a photoinitiator; and optionally about 0.05 to about 25 vol % of a surface cure protection agent. The light-curable resin may configured to be cured responsive to the activation trigger. Curing may include undergoing a phase change, undergoing a state change, or transitioning from a relatively free-formed state to a hardened state. A sheath or coating may be disposed around a photocurable composite of any embodiment herein, where the sheath or coating may be configured to be permeable to the light activation trigger. The sheath or coating may be have an $O_2$ permeability as measured by Oxygen Transmission Rate (OTR; expressed in cc/m$^2$/day) at 23° C. and 0% relative humidity of lower than 500, preferably lower than 100, preferably lower than 80, even more preferably lower than 40. For example, the sheath or coating may have an $O_2$ permeability of about 0.01 to about 100, such as about 0.05 to about 0.2 (e.g., ethylene vinyl alcohol), or preferably between 15 and 35 (e.g., polyamide), or preferably between 40 and 80 (e.g., polyethylene terephthalate). Where a sheath or coating is not disposed around a photocurable composite of any embodiment herein, the photocurable composite preferably include the surface cure protection agent. The filler material preferably transmits light.

In the soft state, the light-curable resin may be conformable (e.g., liquid, gel, or other non-solid). The light-curable resin of the photocurable composite may be in a conformable state, such as a fluid, liquid, putty-like, sculptable, gel-like, or other flowable state (e.g., a flowable state in which shape changes of the light-curable material are mechanically reversible). For example, in the soft state, the light-curable resin may be flowable, while filler material may be solid but flexible. In the hardened state, the light-curable device may be hardened (e.g., solid, stiff, rigid, rubber-like, or other hardened state for reinforcement). The activation trigger may be light, such as light having a selected or desired wavelength or range of wavelengths which cause the transition from the soft state to the hardened state. In the soft state, the photocurable composite may conform to a limb or other injured body part, while in the second state, the photocurable composite may provide fixation to reinforcement and protect a limb or other injured body part of a subject.

Systems and methods including photocurable composites according to the present technology may advantageously improve over existing systems by reducing the time required for the transition to a hardened state, while also providing greater flexibility for conforming or otherwise applying to a region of the body targeted for treatment. For example, systems and methods including a photocurable composite according to the present technology may provide conformability and protection specific to each patient, injury, and/or use case. Where the activation device is an LED-based device configured to output ultraviolet (UV) light, the present technology may improve over existing systems by having a relatively limited bandwidth, making the light-curable device safer to use with biological tissue. Where the light-curable device includes a sheath component configured to be permeable to UV light, the present technology may improve over existing systems by providing protection from unnecessary chemical exposure in an easy-to-use and activate form factor.

In addition, a photocurable composite of the present technology may provide improved device molding and fixation procedure through target targeting. For example, a photocurable composite of the present technology may be activated such that only a portion of the photocurable composite hardens through site-specific exposure of activating light. As current technologies (i.e., not of the present technology) typically harden uniformly, the present technology provides an improvement to deliver sequential and selective reinforcement across complex fracture injuries that may span multiple joints. Moreover, the preset technology may advantageously improve over existing systems by allowing for triggered hardening of the device once the device has been molded to the patient. Conventional technologies that require heating or wetting are activated prior to patient contact. The current technology presents an advantage as the photocurable composite may be shaped on the patient prior to activation, allowing for as much or as little time for shaping prior to activation as desired for the procedure.

As discussed above, the light-curable resin includes about 50 vol % to about 99 vol % (based on the volume of the light-curable resin) of an acrylate-functionalized oligomer, wherein the backbone of the oligomer comprises a polyurethane, a polyether, a polyester, or a combination of any two or more thereof. Thus, the amount of acrylate-functionalized oligomer may be about 50 vol %, about 55 vol %, about 60 vol %, about 65 vol %, about 70 vol %, about 75 vol %, about 80 vol %, about 85 vol %, about 90 vol %, about 95 vol %, about 98 vol %, about 99 vol %, or any range including and/or in between any two of these values. Commercial examples of such acrylate-funcationalized oligomers include, but are not limited to, SOLAREZ 3-D Printing Resin, SOLAREZ Low-Lite, SOLAREZ Low-VOC Dual-Cure Polyester Resin, and SOLAREZ Acrylic Modified Polyester Resin. The acrylate-functionalized oligomer(s) may be selected based on factors including primary mechanical properties for the material. The weight average molecular weight for the acrylate-functionalized oligomer may be about 1,000 Da to about 100,000 Da; thus, the weight average molecular weight for the acrylate-functionalized oligomer may be about 1,000 Da, about 2,000 Da, about 3,000 Da, about 4,000 Da, about 5,000 Da, about 6,000 Da, about 7,000 Da, about 8,000 Da, about 9,000 Da, about 10,000 Da, about 15,000 Da, about 20,000 Da, about 25,000 Da, about 30,000 Da, about 35,000 Da, about 40,000 Da, about 50,000 Da, about 60,000 Da, about 70,000 Da, about 80,000 Da, about 90,000 Da, about 100,000 Da, or any range including and/or in between any two of these values. For example, the weight average molecular weight for the acrylate-functionalized oligomer may be about 9,000 Da to about 15,000 Da.

The light-curable resin includes about 1 vol % to about 50 vol % (based on the volume of the light-curable resin) of a radical-reactive diluent; thus, the amount of radical-reactive diluent may be about 1 vol %, about 1.5 vol %, about 2 vol %, about 2.5 vol %, about 3 vol %, about 3.5 vol %, about 4 vol %, about 4.5 vol %, about 5 vol %, about 8 vol %, about 10 vol %, about 12 vol %, about 14 vol %, about 16 vol %, about 18 vol %, about 20 vol %, about 22 vol %, about 24 vol %, about 26 vol %, about 28 vol %, about 30 vol %, about 32 vol %, about 34 vol %, about 36 vol %, about 38 vol %, about 40 vol %, about 45 vol %, about 50 vol %, or any range including and/or in between any two of these values. Reactive diluents in photocurable systems are well-known to a person of ordinary skill in the art. A "radical-reactive diluent" is a reactive diluent that polymerizes in the light-curable resin along with the acrylate-functionalized oligomer upon activation. The radical-reactive diluents may be employed to lower the viscosity of the resin in the soft state as well as provide options for further tuning of the final properties of the photocurable composite upon hardening. In any embodiment herein, it may be the light-curable resin is substantially free of reactive diluents that are not radical reactive. In any embodiment herein, it may be the photocurable composite is substantially free of reactive diluents that are not radical reactive.

Such radical-reactive diluents include monofunctional monomers, difunctional monomers, and trifunctional monomers. Monofunctional monomers include, but are not limited to, acrylates, methacrylate, cyanoacrylates, and alkyl vinyl ethers. For example, acrylates include, but are not limited to, acrylic acid, methyl acrylate, ethyl acrylate, n-propyl acrylate, isopropyl acrylate, n-butyl acrylate (BA), n-decyl acrylate, isobutyl acrylate, n-amyl acrylate, n-hexyl acrylate, isoamyl acrylate, 2-hydroxyethyl acrylate, 2-hydroxypropyl acrylate, N,N-dimethylaminoethyl acrylate, N,N-diethylaminoethyl acrylate, t-butylaminoethyl acrylate, 2-sulfoethyl acrylate, trifluoroethyl acrylate, glycidyl acrylate, benzyl acrylate, allyl acrylate, 2-n-butoxyethyl acrylate, 2-chloroethyl acrylate, sec-butyl-acrylate, tert-butyl acrylate, 2-ethylbutyl acrylate, cinnamyl acrylate, crotyl acrylate, cyclohexyl acrylate, cyclopentyl acrylate, 2-ethoxyethyl acrylate, furfuryl acrylate, hexafluoroisopropyl acrylate, methallyl acrylate, 3-methoxybutyl acrylate, 2-methoxybutyl acrylate, 2-nitro-2-methylpropyl acrylate, n-octylacrylate, 2-ethylhexyl acrylate, 2-phenoxyethyl acrylate, 2-phenylethyl acrylate, phenyl acrylate, propargyl acrylate, tetrahydrofurfuryl acrylate, tetrahydropyranyl acrylate, or combinations of any two or more thereof. Exemplary difunctional monomers include, but are not limited to, dipropylene glycol diacrylate, tripropylene glycol diacrylate, dipentaerythritol penta/hexa acrylate, dipentaerythritol penta/hexa acrylate, hexanediol diacrylate, or a combination of any two or more thereof. Exemplary trifunctional monomers include, but are not limited to, trimethylolpropane triacrylate.

The light-curable resin includes about 0.05 vol % to about 25 vol % (based on the volume of the light-curable resin) of a surface cure protection agent. Thus, the amount of surface cure protection agent in the light-curable resin may be about 0.05 vol %, about 0.1 vol %, about 0.2 vol %, about 0.3 vol %, about 0.4 vol %, about 0.5 vol %, about 0.6 vol %, about 0.7 vol %, about 0.8 vol %, about 0.9 vol %, about 1 vol %, about 1.1 vol %, about 1.2 vol %, about 1.3 vol %, about 1.4 vol %, about 1.5 vol %, about 1.6 vol %, about 1.7 vol %, about 1.8 vol %, about 1.9 vol %, about 2 vol %, about 5 vol %, about 8 vol. %, about 10 vol. %, about 12 vol %, about 14 vol %, about 16 vol %, about 18 vol %, about 20 vol %, about 22 vol %, about 24 vol %, about 25 vol %, or any range including and/or in between any two of these values. Such surface cure protection agents mitigate oxygen reaction inhibition and include compounds containing sulfur (thiols), nitrogen (amines), or oxygen (ethers) that may react with peroxy radicals. Use of polyethers is preferred as they lack the smell of thiols and the yellowing of amines. Other surface cure protection agents, such as waxes and surfactants (e.g., fluorinated surfactants, silicone surfactants) may partition to the interphase between the light-curable resin and air effectively reducing oxygen transport into the light-curable resin. Surface cure protection agents include, but are not limited to, a mercapto modified polyester acrylate, an amine modified polyester acrylate, a wax, a surfactant, or a combination of any two or more thereof. Exemplary waxes include, but are not limited to, shellac, rosin, morpholine, carnauba wax, polyethylene, polypropylene, beeswax, candelilla wax, microcrystalline wax, and $C_{16}$-$C_{30}$ n-paraffins. Exemplary surfactants include, but are not limited to, sodium laureth sulfate, sodium lauryl suflate, sorbitan sesquioleate, sorbitan dioleate, sorbitan trioleate, pentaerythritol dioleate, pentaerythritol trioleate, silicone ether acrylate surfactants, and silicone polyether acrylate surfactants.

The photoinitiators in the light-curable resin are configured to initiate the polymerization reaction responsive to receiving the activation trigger from the activation device, such as an output of light. The photoinitiators may be configured based on factors such as absorption spectrum, chemical structure, and percent composition within the light-curable resin (e.g., within the photocurable composite), to affect depth and speed of cure.

The light-curable resin may include (1) free radical-based photoinitiators, (2) cation-based photoinitiators, and (3) combinations of (1) & (2). Free radical-based photoinitiators may initiate polymerization of monomers such as acrylates and/or unsaturated polyesters. Cation-based photoinitiators may promote polymerization of multi-functional epoxides, oxetanes, and vinyl ethers. One of the advantages to using cationic systems is that once the polymerization has begun the polymerization is no longer sensitive to $O_2$. Cation systems include a cationic photoinitiator. Exemplary cationic photoinitiators include, but are not limited to, an onium salt, an organometallic compound, and a pyridinium salt. Onium salts may be iodonium salts, sulfonium salts, ammonium salts, phosphonium salts, or a mixture of any two or more thereof.

In any embodiment herein, photoinitiators may be based on free radical chemistry, and a number of different material classes may be implemented for this purpose. It will be appreciated that small concentrations of photoinitiators may be advantageous, as large concentrations of photoinitiators may limit cure of the resin system. For example, a concentration of photoinitiators may be determined based on factors such as a total time required for the light-curable device to transition from the soft state to the hardened state and an amount of the light-curable material which undergoes curing responsive to the activation trigger. About 0.001 vol % to about 2 vol % (based on the volume of the light-curable resin) of a photoinitiator is typically included in the light-curable resin. Thus, the amount of photoinitiator in the in the light-curable resin may be about 0.001 vol %, about 0.005 vol %, about 0.01 vol %, about 0.05 vol %, about 0.1 vol %, about 0.2 vol %, about 0.3 vol %, about 0.4 vol %, about 0.5 vol %, about 0.6 vol %, about 0.7 vol %, about 0.8 vol %, about 0.9 vol %, about 1 vol %, about 1.1 vol %, about 1.2 vol %, about 1.3 vol %, about 1.4 vol %, about 1.5 vol %, about 1.6 vol %, about 1.7 vol %, about 1.8 vol %, about 1.9 vol %, about 2 vol %, or any range including and/or in between any two of these values. For example, sample concentrations of photoinitiators include but are not limited to be less than or equal to about 0.01% by volume, be greater than about 0.01% and less than about 0.1% by volume, be greater than about 0.1% by volume and less than about 1% by volume or be greater than about 1% and less about 2% by volume. Photoinitiator may be added as a liquid, a powder, a solid suspended in a liquid, or a mix of more than one chemical.

Exemplary photoinitiators include, but are not limited to:
Class: α-Hydroxyketone
  IRGACURE 184 (1-Hydroxy-cyclohexyl-phenyl-ketone)
  IRGACURE 500 (IRGACURE 184 and Benzophenone)
  DAROCUR 1173 (2-Hydroxy-2-methyl-1-phenyl-1-propanone)
  IRGACURE 2959 (2-Hydroxy-1-[4-(2-hydroxyethoxy) phenyl]-2-methyl-1-propanone)
Class: Phenylglyoxylate
  DAROCUR MBF (Methylbenzoylformate)
  IRGACURE 754 (oxy-phenyl-acetic acid 2-[2 oxo-2 phenyl-acetoxy-ethoxy]-ethyl ester and oxy-phenyl-acetic 2-[2-hydroxy-ethoxy]-ethyl ester)
Class: Benzyldimethyl-ketal
  IRGACURE 651 (Alpha, alpha-dimethoxy-alpha-phenylacetophenone)
Class: α-Aminoketone
  IRGACURE 369 (2-Benzyl-2-(dimethylamino)-1-[4-(4-morpholinyl) phenyl]-1-butanone)
  IRGACURE 907 (2-Methyl-1-[4-(methylthio)phenyl]-2-(4-morpholinyl)-1-propanone)
  IRGACURE 1300 (IRGACURE 369 (30 wt %)+IRGACURE 651 (70 wt %))
Class: Mono Acyl Phosphine (MAPO)
  DAROCUR TPO (Diphenyl (2,4,6-trimethylbenzoyl)-phosphine oxide)
Class: MAPO/α-Hydroxyketone
  DAROCUR 4265 (DAROCUR TPO (50 wt %)+DAROCUR 1173 (50 wt %))
Class: Bis Acyl Phosphine (BAPO)
  IRGACURE 819 (Phosphine oxide, phenyl bis (2,4,6-trimethyl benzoyl))
Class: BAPO Dispersion
  IRGACURE 819DW (IRGACURE 819 (45% active) dispersed in water
Class: BAPO/α-Hydroxyketone
  IRGACURE 2022 (IRGACURE 819 (20 wt %)+DAROCUR 1173 (80 wt %))
Class: Phosphine oxide
  IRGACURE 2100 (phosphine oxide)
Class: Metallocene
  IRGACURE 784 (Bis (eta 5-2,4-cyclopentadien-1-yl) Bis [2,6-difluoro-3-(1H-pyrrol-1-yl)phenyl]titanium)

In any embodiment herein, multiple photoinitiators may be used to encourage different cure characteristics. The light-curable material (e.g., resin) may be a single-part system, such that the light-curable material need not be mixed with an additional reactant before use. The light-curable material may be configured to be cured to a range of depths. The light-curable resin may include or be provided with inhibitors or activators configured to increase or decrease a rate of the chemical reaction (e.g., polymerization reaction) associated with the transition from the first (soft) state to the second (hardened) state. In any embodiment herein, the light-curable resin may be configured to polymerize upon exposure to light with a wavelength from about 280 nm to about 700 nm, preferably a wavelength from about 280 nm to about 400 nm, even more preferably a wavelength from about 315 nm to about 400 nm.

The photocurable composite includes a filler material where the light-curable resin may be disposed within the filler material. The filler material may be configured to transmit light. The photocurable composite may include 1, 2, 3, 4, 5, 6, 7, 8, 9, 10, or more layers (also referred to as plys or sheets). The filler material may be or include a glass mat, glass fibers, glass fabric (fiberglass, e.g., E-Glass) fiberglass fibers, fiberglass knit fabrics, cellulose nanocrystals, silica, or a combination of any two or more thereof. The thickness of the filler material may be about 0.001 inches to about 0.1 inches for each layer of filler material. Thus, the thickness of the filler material (for each layer, if more than one layer) in inches may be about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, about 0.1, or any range including and/or in between any two of these values. For example, the photocurable composite may include about 1 to about 6 layers of filler material where each layer is about 0.03 inches thick. The density of the filler material may be about 0.005 $g/in^2$ to about 1 $g/in^2$; the filler material may be at a density in $g/in^2$ of about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, or any range including and/or in between any two of these values. For example, the density of the filler material may be about 0.01 $g/in^2$ to about 0.5 $g/in^2$. Fillers may be woven, netted, dispersed, or otherwise, embedded in the light-curable material. Composite fillers may be pre-impregnated with the light-curable material such that the fibers are completely covered with the light-curable material. Bonding agents or additives may be used to help promote adhesion of the resin system to the filler.

The light-curable resin may be disposed within the filler material. The photocurable composite may include about 20 wt. % to about 60 wt. % light-curable resin based on total weight of the composite. Thus, the amount of light-curable resin in the photocurable composite may be about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %. about 56 wt. %, about 58 wt. %, about 60 wt. %, or any range including and/or in between any two of these values.

The photocurable composite, upon hardening due to activation, may provide the strength, conformability, and ruggedness necessary to comfortably stabilize a fracture or other injury to a body part. Photocurable composites of the present technology may be cured in open air or in light transparent (e.g., UV-transparent) removable molds. A sheath component, which may enclose, encapsulate, surround, or otherwise be disposed around the light-curable material, may advantageously make the photocurable composite usable without gloves and waste free. Further, the sheath component may provide a barrier to mass transfer from outside the photocurable composite to the light-curable resin, particularly a barrier to oxygen ($O_2$) transfer, preventing oxygen inhibition of the polymerization reaction.

In any embodiment herein, an outer layer of the sheath (which may be open to the air) may be translucent to light such that UV light or any other wavelength range needed to cure the light-curable resin may penetrate the sheath and cure photocurable composite. The inner layer of the sheath may be opaque to block unwanted radiation reaching the skin. Either the inner and/or the outer layers may act as a heat barrier to reduce the temperature applied to the skin due to the polymerization reaction when curing. The sheath may be configured to provide a moisture and/or oxygen barrier. The sheath may be in the form of a separate layer, a bonded, layer, a coating, or multiple layers or coatings. The sheath or coating may be a permanent part of the photocurable composite or it may be removable. The sheath may be opaque, or otherwise have no or relatively low permeability or transmissivity for light, such that any light or radiation contained within the photocurable composite stays inside to continue the curing process.

The activation device, such as a UV light source, may be a mercury lamp, or an LED device (e.g., UV LEDs configured to output light in the UV-A spectrum, such as from about 315 nm to 400 nm, from 300 nm to 415 nm, or more specific wavelength ranges within the range of 315 nm to 400 nm). The types of light include but are not limited to: the UV spectrum through the visible light spectrum (e.g., $\lambda$=260-700 nm), or UV-A and/or visible blue light (a wavelength range may be 315 nm-450 nm). For example, a typical photocurable composite of the present technology may cure at $\lambda$=375 nm. In any embodiment herein, the photocurable composite may be configured to be curable without harming human tissue during the application of the device.

The photocurable composite may be configured for use with a traditional cast liner, padding, or stockinet. In any embodiment herein, photocurable composite may be configured for use with traditional removal devices like a cast saw. The photocurable composite may be configured for use with additional added straps, buckles, Velcro, or closure devices to aid in device conformability to the injury or patient and/or better fit. These strap etc. may be elastic or non-elastic. The light-curable resin may change color or transparency to indicate depth of cure or complete cure. The photocurable composite may be provided in a preformed configuration optimized for a particular injury type in a subject, body part, anatomical size, or other characteristic. Alternatively, the materials may be manufactured into generic shapes such as tape or sheets meant to be divided into smaller usable sections via cutting, perforations, dispenser, or used as a whole section. In embodiments that do not include a sheath as described herein, the photocurable composite may be fabricated in cuttable rolls and sheets.

In a related aspect, a kit is provided that includes a light-curable resin of any embodiment described herein as well as instructions for generating a photocurable composite of any embodiment described herein. The kit may further include a filler material of any embodiment as described herein. The filler material may be separate from the light-curable resin. The instructions may include instructions for combining a filler material with the light-curable resin to provide the photocurable composite with about 20 wt. % to about 60 wt. % light-curable resin (or any value/subrange as described above). The kit may be a portable kit. For example, the portable kit may be sized to have a relatively small form factor, lightweight design, etc., for storing and/or travelling. The portable kit may have a total weight less than a threshold weight (e.g., less than or equal to 5 pounds, less than 2 pounds, less than 1 pounds, or less than any other weight between about 0 and 5 pounds). The portable kit may be sized to fit inside of a backpack or other travelling case. For example, the portable kit may be sized for use by users from ski patrols treating broken ankles on mountaintops to medical professionals who travel to remote locations.

In a further related aspect, a method is provided that includes exposing a photocurable composite of any embodiment described herein to a wavelength of light from about 280 nm to about 700 nm to provide a hardened material (i.e., the hardened photocurable composite). The exposing may include emission of the light from an artificial light source (any one or more of the sources described herein) and/or from the sun. The exposing may or may not include a wavelength of light from about 380 nm to about 700 nm. In any embodiment herein, the exposing may include a wavelength of light from about 280 nm to 315 nm, about 315 nm to about 375 nm, or a combination thereof. The molding may include taking one or more rolls of the photocurable composite and unrolling the roll in order to wrap the photocurable composite around the extremity of the subject.

In a yet further related aspect, a method is provided immobilizing a fracture of a subject, where the method includes molding a photocurable composite of any embodiment described herein around an extremity of a subject that includes a fractured bone to provide a molded composite and exposing the molded composite to a wavelength of light from about 280 nm to about 700 nm to provide a hardened material. The exposing may include emission of the light from an artificial light source (any one or more of the sources described herein) and/or from the sun. The exposing may or may not include a wavelength of light from about 380 nm to about 700 nm. In any embodiment herein, the exposing may include a wavelength of light from about 280 nm to 315 nm, about 315 nm to about 375 nm, or a combination thereof.

The light-curable resin of the photocurable composite may be exposed to light in various ways. The photocurable composite may be exposed to ambient light that would cure the photocurable composite from the outside-in. In this case the light may hit the photocurable composite directly and/or filter through the sheath. The photocurable composite may be exposed to an external concentrated source (e.g., a lamp, a wand, a lighted container, a flashlight, a lighted pad, dispenser, bulb, an enclosed space, etc.). Prior to use, the photocurable composite may be stored away from ambient light to prevent pre-use hardening. The photocurable composite may be packed in aluminum foil or otherwise light opaque bag which may be heat sealed. Material may be vacuum packed on nitrogen to reduce amount of oxygen in contact with light-curable resin.

The activation trigger may be exposure to ambient light or other radiation (e.g., UV light). A dispenser may output light energy as the activation trigger. For example, the dispenser may include a UV light device positioned adjacent to a tape or sheet of the photocurable composite that may be activated in response to activation of the UV light device. The light-curable resin may receive UV light from a light source remote from the photocurable composite (e.g., a remote point source, the environment, etc.). In any embodiment herein, the light energy for an activation trigger may come from a special chamber in which the photocurable composite or the site of injury covered in the photocurable composite is placed, as part of the sheath where it is activated by a user, etc.

The state change occurs relatively quickly. For example, the state may occur within seconds or minutes of the activation trigger (e.g., less than 0.1 s, less than 1 s, less than 1 min, less than 10 min, less than 15 min, etc.).

The activation device may include one or more controllable LEDs, which may be varied in orientation, number of units, shape of package, focus, filter, spread, and/or power variation. The activation device is configured to generate, transmit, output, or otherwise provide a light-based activation trigger, such as light in the UV-A spectrum, to cause the light-curable resin of the photocurable composite to transition from the soft state to the hardened state. For example, the activation trigger may cause the light-curable resin to polymerize and harden on the order of minutes, as opposed to half an hour or longer for existing cast systems.

In various embodiments, an external concentrated source may be in the form of a portable device, a table mount, a floor mount, a wall-mount or a free-standing device. The source may use irradiance ranges including but not limited to 0.001-150 W/m². The source may be shielded to prevent unwanted exposure to eyes and skin. The source may be directed, concentrated, diffused, or filtered to promote selective curing, curing with limited bandwidth, or even curing across a large area. The source may have a specified warm up time. The source may have LEDs in a variety of configuration in order to promote even curing. The source may use different kinds of LEDs at the same time (e.g., each with multiple wavelengths) in order to promote different kinds of curing. The source may vary the power directed to different LEDs during use (e.g., ramping LED intensity up and down) in order to promote better curing. The source might have an associated mount, alignment guide, etc. that may help position a patient into the right orientation for treatment/cure.

The sheath component, or materials thereof, may be configured to be flexible and UV transparent (have a high UV transmission efficiency) as well as remain UV stable during the procedure and use of the photocurable composite. Sample materials for this component include but are not limited to films, coatings, fabrics, etc. of silicone, polyurethane, PMMA (polymethylmethacrylate), polycarbonate, optical nylon, glass, and epoxy.

In an exemplary implementation, the photocurable composite may include the following formulations & components:

Resin system: Monomer 1 25% SR833S (Sartomer), Monomer 2 25% SR531, Oligomer CN133 (Sartomer) 50%
Photoinitiator EPX-0286 (Essetech)
Filler: 4 ply E-Fiberglass, 0.02 inches thickness per ply,
Sheath: water-clear silicone coating
Source: 365 nm LED source with 100 W/m^2 peak irradiance and diffuser filter An additional exemplary formulation includes untreated raschel-knit fiberglass fabric (Carolina Narrow Fabric Co.) loaded with 50 wt. % SOLAREZ 3 min Acrylic Modified Dual-Cure Polyester Resin (Carolina Narrow Fabric company). This may be in the form of a 3-inch wide strip rolled and packaged within a light-proof pouch.

The photocurable composite may include embedded fillers configured to improve the mechanical properties of the photocurable composite when in the hardened state, or to facilitate or catalyze the transition from the soft state to the hardened state. For example, such filler materials may include particles, beads, fibers, mesh, foam pieces or sheets, fabric, etc. The filler may be an optical fiber or other light-transmitting filler. For example, fibers may be activated at a first end by an internal or external bulb shining with light of the required frequency, which is then transmitted along a length of the fiber. The optical fibers may be scored, cut, notched, or otherwise shaped or configured to transmit light along the entire length of the fiber, or specific locations along the length of the fiber, enabling the optical fibers to induce curing, including selectively inducing curing. Optical fibers may be woven, netted, dispersed, or otherwise embedded in the photocurable composite, such as to facilitate or promote evenly distributed curing.

In some embodiments, the photocurable composite includes, is operatively coupled to, is attached, attachable to, or has embedded electronics to promote activation.

Referring now to FIG. 1, a reinforcement system is shown according to an embodiment. The reinforcement system includes a photocurable composite 100 and an activation device 200. The photocurable composite includes a light-curable resin 110 configured to undergo a transition from a first state (e.g., a conformable state) to a second state (e.g., a cured or hardened state) responsive to an activation trigger. The activation device 200 is configured to output a light-based activation trigger 210, such as UV-A light, to cause the transition from the first state to the second state.

Referring now to FIG. 2A, a procedure for using the photocurable composite 100 is shown according to an embodiment. At 220, the photocurable composite 220 may be pre-stored or received in a container 102. The container 102 may be configured to block light (e.g., has relatively high reflectivity and/or relatively low transmissivity) from reaching the photocurable composite 220 while photocurable composite 220 is stored. At 222, the photocurable composite 100 may be applied to a body part 101 of a patient. For example, due to its conformity in the first state, the photocurable composite 100 may be wrapped around and adjusted to fit to the body part 101 according to the patient's treatment and comfort needs. At 224, the activation device 200 delivers or outputs the light-based activation trigger (e.g., UV-A light) to the photocurable composite 100. The activation trigger is received by light-curable resin of the photocurable composite, causing the photocurable composite 100 to transition to the second state and harden, providing rigidity and support to the body part 101.

Figure 2B:
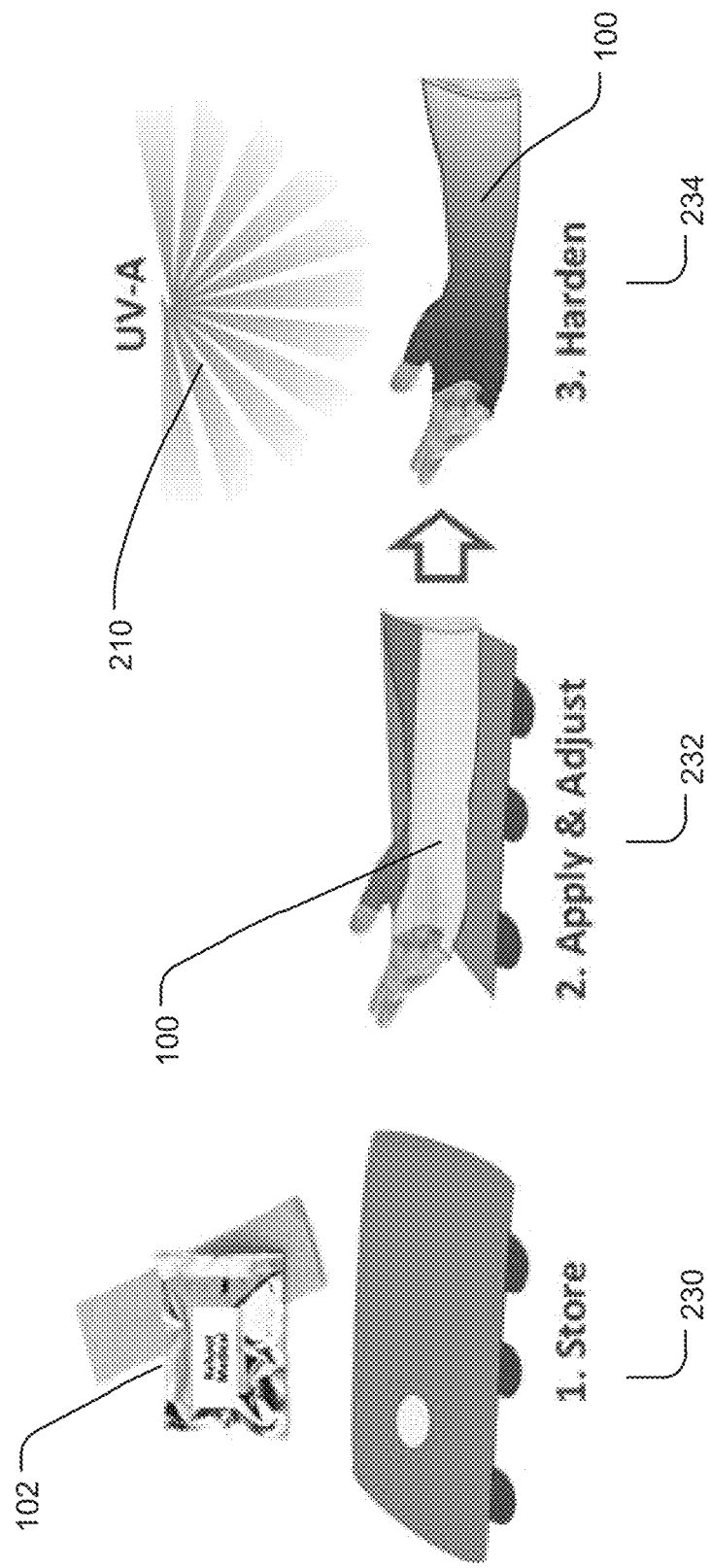

Similarly, referring now to FIG. 2B, at 230, the photocurable composite may be received in a container 102; at 232, the photocurable composite 100 may be applied and adjusted to the patient; and at 234, the photocurable composite may be caused to transition from the first state to the second state, to undergo curing or hardening, responsive to the activation trigger 210.

Figure 3B:
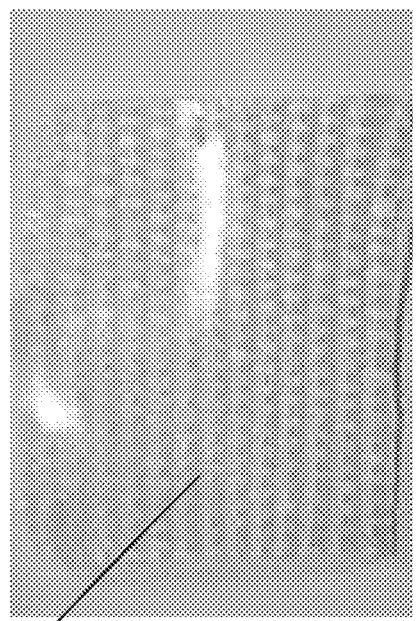
FIGS. 3A-3D illustrate testing and operation of light-curable devices and associated systems, according to embodiments of the present disclosure.
Figure 3D:
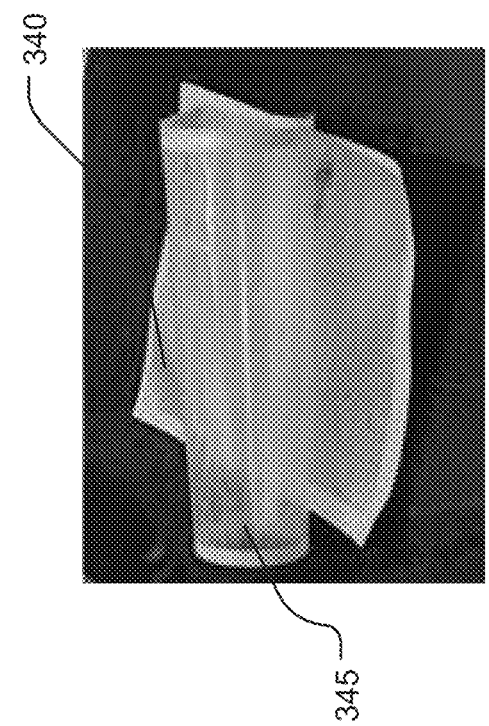
Figure 3A:
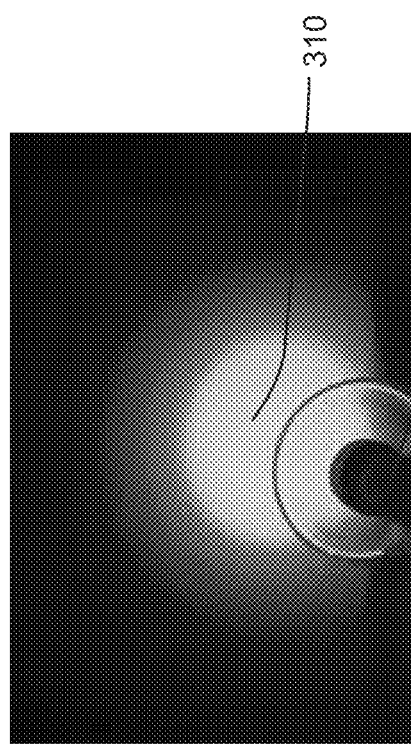
Figure 3C:
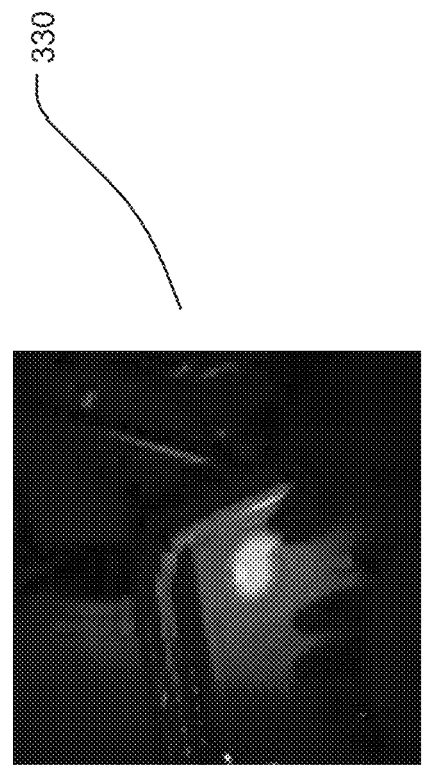

Referring now to FIGS. 3A-3D, various embodiments of photocurable composite and systems are shown according to various embodiments. As shown in FIG. 3A, an activation device 300 may cause output of an activation trigger 310, such as a UV light transmission. As shown in FIG. 3B, a coating material 320 may be configured as a sheath component which is light-permeable, such as by being UV light-permeable. As shown in FIG. 3C, a system 330 may be configured to determine curing times for photocurable composites, such as to facilitate material selection and design. As shown in FIG. 3D, in a first state 340, a photocurable composite may have a sheet- or wrap-shaped conformation; in a second state 345, after undergoing a transition to be hardened or cured, the photocurable composite may be shaped to match or conform to a desired body part to be protected.

Figure 4:
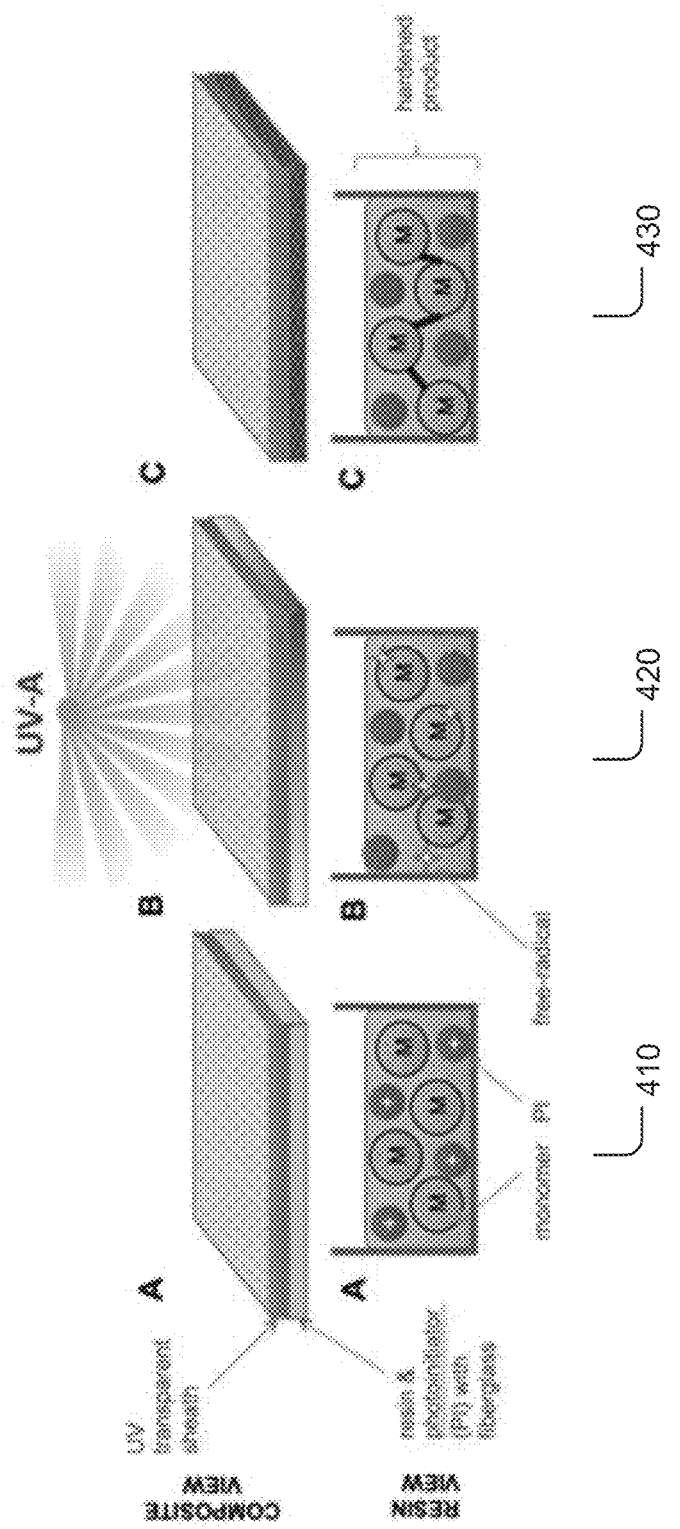
FIG. 4 illustrates schematic diagrams of states of a light-curable device for a transition from an inactivated state to a cured or hardened state, according to embodiments of the present disclosure.

Referring now to FIG. 4, a schematic flow diagram illustrates the transition from the first state to the second state of a photocurable composite according to an embodiment. At 410, in the first state, the photocurable composite may include a UV-transparent sheath component and a light-curable resin of any embodiment described herein. At 420, responsive to receiving a UV-A light-based activation trigger, which passes through the UV-transparent sheath component, the photoinitiators undergo a reaction causing generation or a release of free radicals. At 430, responsive to the action of the free radicals, the light-curable resin undergoes a polymerization reaction, enabling the transition to the second state where the photocurable composite is a hardened or cured device or product.

Figure 5:
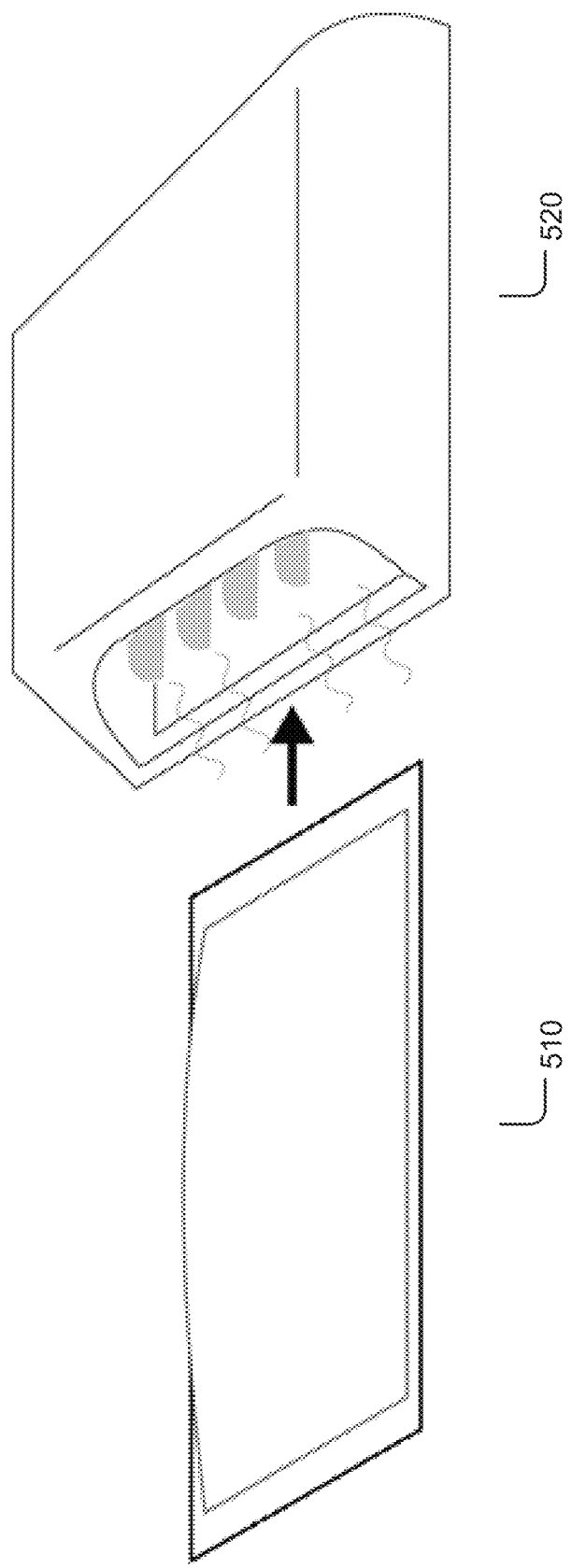
FIGS. 5-7 illustrate various systems and configurations for curing a light-curable device, according to various embodiments of the present disclosure.
Figure 6:
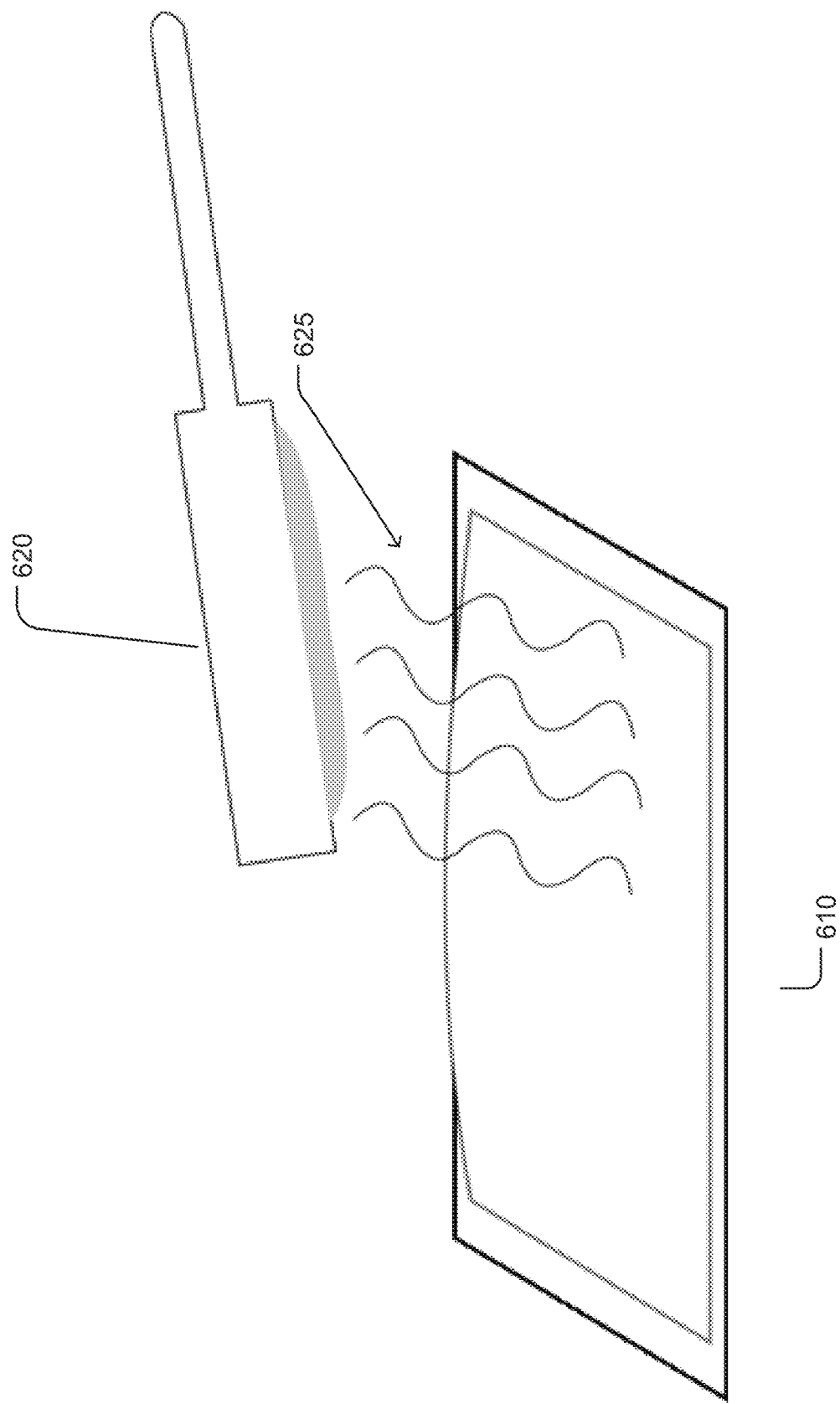

Referring now to FIG. 5, in some embodiments, a photocurable composite 510 according to the present disclosure may be activated by being disposed in a UV-oven 520 (e.g., an oven having a UV lamp). Referring now to FIG. 6, in some embodiments, a photocurable composite 610 according to the present disclosure may be activated by a UV wand 620 configured to generate and output light-based activation trigger 625 (e.g., UV light of a selected bandwidth for causing the photocurable composite 610 to transition to a hardened state).

Figure 7:
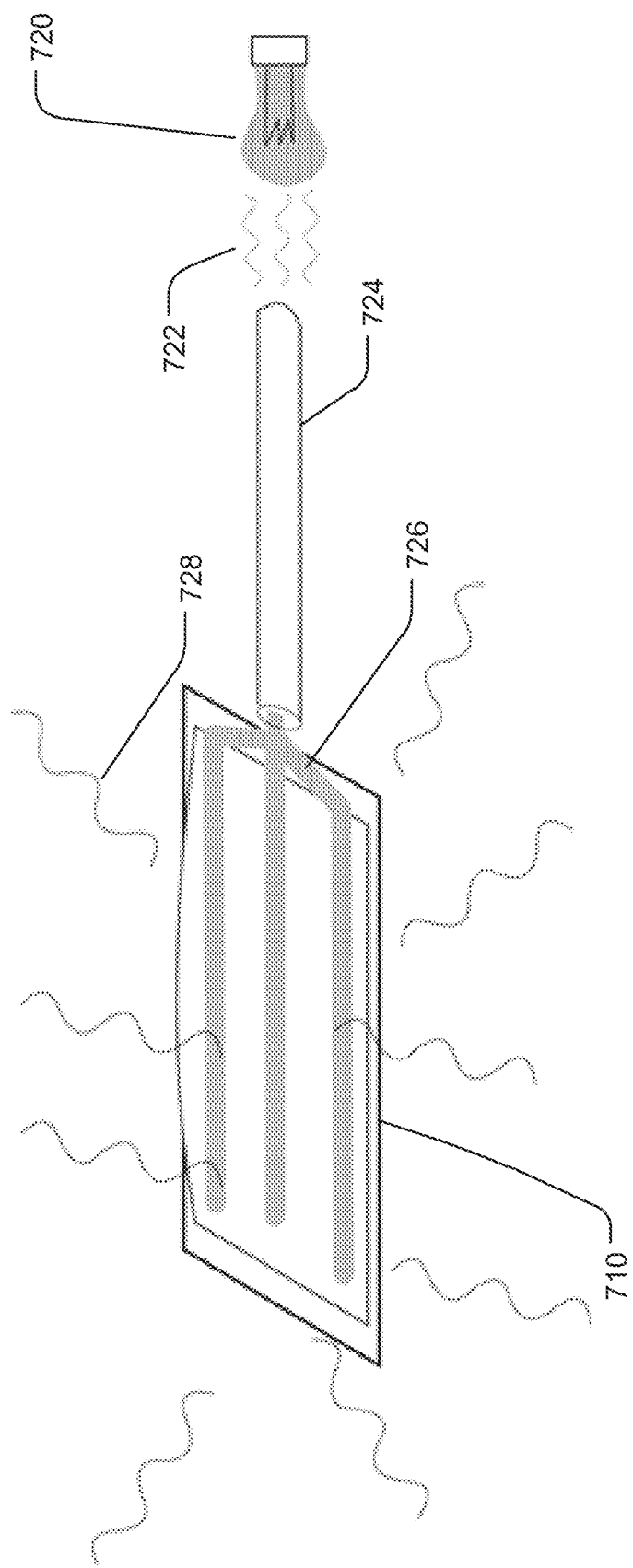

Referring now to FIG. 7, in some embodiments, a photocurable composite 710 may include optical fibers 726. The optical fibers 726 are configured to receive activation trigger light 722 from an activation device 720; the activation trigger light 722 may be received via a channeling device 724. The activation trigger light 722 is output as light 728 by the optical fibers 726, causing the photocurable composite 710 (e.g., light-curable resin within the photocurable composite 710) to transition to the hardened state.

While certain embodiments have been illustrated and described, a person with ordinary skill in the art, after reading the foregoing specification, can effect changes, substitutions of equivalents and other types of alterations to the compounds of the present technology. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A photocurable composite comprising a light-curable resin and a filler material, wherein the light-curable resin comprises
  about 50 vol % to about 99 vol % based on total volume of the light-curable resin of an acrylate-functionalized oligomer, wherein the backbone of the oligomer comprises a polyurethane, a polyether, a polyester, or a combination of any two or more thereof;
  about 1 vol % to about 50 vol % of a radical-reactive diluent;
  about 0.05 vol % to about 2 vol % of a photoinitiator; and
  optionally about 0.05 vol % to about 25 vol % of a surface cure protection agent;
  wherein the filler material optionally transmits visible light, UV-A light, UV-B light, or a combination of any two or more thereof.

B. The photocurable composite of Paragraph A, wherein the acrylate-functionalized oligomer comprises an acrylate-functionalized polyurethane, an acrylate-functionalized polyester, or a combination thereof.

C. The photocurable composite of Paragraph A or Paragraph B, wherein the radical-reactive diluent comprises compounds with two or more radical-reactive groups.

D. The photocurable composite of any one of Paragraphs A-C, wherein radical-reactive diluent comprises dipropylene glycol diacrylate, tripropylene glycol diacrylate, dipentaerythritol penta/hexa acrylate, dipentaerythritol penta/hexa acrylate, or a combination of any two or more thereof.

E. The photocurable composite of any one of Paragraphs A-D, wherein the photoinitiator comprises an α-hydroxyketone, a phenylglyoxylate, a benzyldimethyl ketal, an α-aminoketone, a phosphine oxide, a mono acyl phosphine oxide, a bis acyl phosphine oxide, a metallocene, or a combination of any two or more thereof.

F. The photocurable composite of any one of Paragraphs A-E, wherein the photoinitiator comprises 1-hydroxycyclohexyl phenyl ketone, benzophenone, 2-hydroxy-2-methyl-1-phenyl-1-propanone, 2-hydroxy-1-[4-(2-hydroxyethoxy) phenyl]-2-methyl-1-propanone, methylbenzoylformate, oxy-phenyl-acetic 2-[2 oxo-2 phenyl-acetoxy-ethoxy]-ethyl ester, oxy-phenyl-acetic 2-[2-hydroxy-ethoxy]-ethyl ester, benzyl dimethyl ketal, 2-benzyl-2-(dimethylamino)-1-[4-(4-morpholinyl)phenyl]-1-butanone), 2-methyl-1-[4-(methylthio)phenyl]-2-(4-morpholinyl)-1-propanone), diphenyl (2,4,6-trimethylbenzoyl) phosphine oxide, phenyl bis (2,4,6-trimethyl benzoyl) phosphine oxide, phosphine oxide, bis (eta 5-2, 4-cyclopentadien-1-yl) bis[2,6-difluoro-3-(1H-pyrrol-1-yl)phenyl]titanium, or a combination of any two or more thereof.

G. The photocurable composite of any one of Paragraphs A-F, wherein the surface cure protection agent comprises mercapto modified polyester acrylate; amine modified polyester acrylate, a wax, a surfactant, or a combination of any two or more thereof.

H. The photocurable composite of any one of Paragraphs A-G, wherein the filler material is configured to transmit light.

I. The photocurable composite of any one of Paragraphs A-H, wherein the filler material comprises a glass mat, glass fibers, glass fabric, fiberglass fibers, fiberglass knit fabrics, cellulose nanocrystals, silica, or a combination of any two or more thereof.

J. The photocurable composite of any one of Paragraphs A-I, wherein the composition comprises two or more layers of filler material.

K. The photocurable composite of any one of Paragraphs A-J, wherein a thickness of the filler material is from about 0.001 inches to about 0.1 inches.

L. The photocurable composite of any one of Paragraphs A-K, wherein the density of the filler material is from about 0.005 $g/in^2$ to about 1 $g/in^2$.

M. The photocurable composite of any one of Paragraphs A-L, wherein the light-curable resin is disposed within the filler material.

N. The photocurable composite of any one of Paragraphs A-M, wherein the composite is substantially free of reactive diluents that are not radical-reactive.

O. The photocurable composite of any one of Paragraphs A-N, wherein the composite comprises about 20 wt. % to about 60 wt. % light-curable resin based on total weight of the composite.

P. The photocurable composite of any one of Paragraphs A-O, wherein the light-curable resin is configured to polymerize upon exposure to light with a wavelength from about 280 nm to about 700 nm.

Q. The photocurable composite of any one of Paragraphs A-P, wherein the light-curable resin is configured to polymerize upon exposure to light with a wavelength from about 280 nm to about 400 nm.

R. The photocurable composite of any one of Paragraphs A-Q, wherein the light-curable resin is configured to polymerize upon exposure to light with a wavelength from about 380 nm to about 700 nm.

S. A method comprising
exposing a photocurable composite of any one of Paragraphs A-R to a wavelength of light from about 280 nm to about 700 nm to provide a hardened material, optionally a wavelength of light from about 380 nm to about 700 nm, from about 280 nm to 315 nm, from about 315 nm to about 375 nm, or a combination of any two or more thereof.

T. The method of Paragraph S, wherein the method comprises exposing the photocurable composite to the wavelength of light for a duration of about 0.1 second to about 15 minutes.

U. A kit comprising
a light-curable resin comprising
about 50 vol % to about 99 vol % of an acrylate-functionalized oligomer, wherein the backbone of the oligomer comprises a polyurethane, a polyether, a polyester, or a combination of any two or more thereof;
about 1 vol % to about 50 vol % of a radical-reactive diluent;
about 0.05 vol % to about 2 vol % of a photoinitiator; and
about 0.05 to about 25 vol % of a surface cure protection agent;
optionally a light source; and
instructions for generating a photocurable composite of any one of Paragraphs A-R.

V. The kit of Paragraph U, wherein the kit further comprises a filler material, wherein the filler material optionally transmits visible light, UV-A light, UV-B light, or a combination of any two or more thereof.

W. The kit of Paragraph U or Paragraph V, wherein the kit further comprises a filler material separate from the light-curable resin.

X. The kit of Paragraph V or Paragraph W, wherein two or more layers of filler material are included in the kit.

Y. The kit of any one of Paragraphs V-X, wherein a thickness of the filler material is from about 0.001 inches to about 0.1 inches.

Z. The kit of any one of Paragraphs V-Y, wherein the density of the filler material is from about 0.005 $g/in^2$ to about 1 $g/in^2$.

AA. The kit of any one of Paragraphs V-Z, wherein the instructions direct including about 20 wt. % to about 60 wt. % light-curable resin based on total weight of the composite.

AB. The kit of any one of Paragraphs U-AA, wherein the light-curable resin is configured to polymerize upon exposure to light with a wavelength from about 280 nm to about 700 nm.

AC. The kit of any one of Paragraphs U-AB, wherein the light-curable resin is configured to polymerize upon exposure to light with a wavelength from about 280 nm to about 400 nm.

AD. The kit of any one of Paragraphs U-AC, wherein the light-curable resin is configured to polymerize upon exposure to light with a wavelength from about 380 nm to about 700 nm.

AE. The kit of any one of Paragraphs U-AD, wherein the acrylate-functionalized oligomer comprises an acrylate-functionalized polyurethane, an acrylate-functionalized polyester, or a combination thereof.

AF. The kit of any one of Paragraphs U-AE, wherein the radical-reactive diluent comprises compounds with two or more radical-reactive groups.

AG. The kit of any one of Paragraphs U-AF, wherein radical-reactive diluent comprises dipropylene glycol diacrylate, tripropylene glycol diacrylate, dipentaerythritol penta/hexa acrylate, dipentaerythritol penta/hexa acrylate, or a combination of any two or more thereof.

AH. The kit of any one of Paragraphs U-AG, wherein the photoinitiator comprises an α-hydroxyketone, a phenylglyoxylate, a benzyldimethyl ketal, an α-aminoketone, a phosphine oxide, a mono acyl phosphine oxide, a bis acyl phosphine oxide, a metallocene, or a combination of any two or more thereof.

AI. The kit of any one of Paragraphs U-AH, wherein the photoinitiator comprises 1-hydroxy-cyclohexyl phenyl ketone, benzophenone, 2-hydroxy-2-methyl-1-phenyl-1-propanone, 2-hydroxy-1-[4-(2-hydroxyethoxy) phenyl]-2-methyl-1-propanone, methylbenzoylformate, oxy-phenyl-acetic 2-[2 oxo-2 phenyl-acetoxy-ethoxy]-ethyl ester, oxy-phenyl-acetic 2-[2-hydroxy-ethoxy]-ethyl ester, benzyl dimethyl ketal, 2-benzyl-2-(dimethylamino)-1-[4-(4-morpholinyl)phenyl]-1-butanone), 2-methyl-1-[4-(methylthio)phenyl]-2-(4-morpholinyl)-1-propanone), diphenyl (2,4,6-trimethylbenzoyl) phosphine oxide, phenyl bis (2,4,6-trimethyl benzoyl) phosphine oxide, phosphine oxide, bis(eta 5-2,4-cyclopentadien-1-yl) bis[2,6-difluoro-3-(1H-pyrrol-1-yl)phenyl]titanium, or a combination of any two or more thereof.

AJ. The kit of any one of Paragraphs U-AI, wherein the surface cure protection agent comprises mercapto modified polyester acrylate; amine modified polyester acrylate, a wax, a surfactant, or a combination of any two or more thereof.

AK. A method of immobilizing a fracture of a subject, the method comprising
molding a photocurable composite of any one of Paragraphs A-R around an extremity of a subject to provide a molded composite; and
exposing the molded composite to a wavelength of light from about 280 nm to about 700 nm to provide a hardened material, optionally a wavelength of light from about 380 nm to about 700 nm, from about 280 nm to 315 nm, from about 315 nm to about 375 nm, or a combination of any two or more thereof.

Other embodiments are set forth in the following claims, along with the full scope of equivalents to which such claims are entitled.

What is claimed is:

1. A photocurable composite comprising a light-curable resin and a filler material, wherein the light-curable resin comprises
    about 50 vol % to about 99 vol % based on total volume of the light-curable resin of an acrylate-functionalized oligomer, wherein the backbone of the oligomer comprises a polyurethane, a polyether, a polyester, or a combination of any two or more thereof;
    about 1 vol % to about 50 vol % of a radical-reactive diluent;
    about 0.05 vol % to about 2 vol % of a photoinitiator; and
    optionally about 0.05 vol % to about 25 vol % of a surface cure protection agent wherein radical-reactive diluent comprises dipropylene glycol diacrylate, tripropylene glycol diacrylate, dipentaerythritol penta/hexa acrylate, dipentaerythritol penta/hexa acrylate, or a combination of any two or more thereof.

2. The photocurable composite of claim 1, wherein the acrylate-functionalized oligomer comprises an acrylate-functionalized polyurethane, an acrylate-functionalized polyester, or a combination thereof.

3. The photocurable composite of claim 1, wherein the photoinitiator comprises an α-hydroxyketone, a phenylglyoxylate, a benzyldimethyl ketal, an α-aminoketone, a phosphine oxide, a mono acyl phosphine oxide, a bis acyl phosphine oxide, a metallocene, or a combination of any two or more thereof.

4. The photocurable composite of claim 1, wherein the photoinitiator comprises 1-hydroxy-cyclohexyl phenyl ketone, benzophenone, 2-hydroxy-2-methyl-1-phenyl-1-propanone, 2-hydroxy-1-[4-(2-hydroxyethoxy) phenyl]-2-methyl-1-propanone, methylbenzoylformate, oxy-phenyl-acetic 2-[2 oxo-2 phenyl-acetoxy-ethoxy]-ethyl ester, oxy-phenyl-acetic 2-[2-hydroxy-ethoxy]-ethyl ester, benzyl dimethyl ketal, 2-benzyl-2-(dimethylamino)-1-[4-(4-morpholinyl)phenyl]-1-butanone), 2-methyl-1-[4-(methylthio)phenyl]-2-(4-morpholinyl)-1-propanone), diphenyl (2,4,6-trimethylbenzoyl) phosphine oxide, phenyl bis (2,4,6-trimethyl benzoyl) phosphine oxide, phosphine oxide, bis (eta 5-2,4-cyclopentadien-1-yl) bis[2,6-difluoro-3-(1H-pyrrol-1-yl)phenyl]titanium, or a combination of any two or more thereof.

5. The photocurable composite of claim 1, wherein the surface cure protection agent comprises mercapto modified polyester acrylate, amine modified polyester acrylate, a wax, a surfactant, or a combination of any two or more thereof.

6. The photocurable composite of claim 1, wherein the filler material is configured to transmit light.

7. The photocurable composite of claim 1, wherein the filler material comprises a glass mat, glass fibers, glass fabric, fiberglass fibers, fiberglass knit fabrics, cellulose nanocrystals, silica, or a combination of any two or more thereof.

8. The photocurable composite of claim 1, wherein the composition comprises two or more layers of filler material.

9. The photocurable composite of claim 1, wherein the composite is substantially free of reactive diluents that are not radical-reactive.

10. The photocurable composite of claim 1, wherein the composite comprises about 20 wt. % to about 60 wt. % light-curable resin based on total weight of the composite.

11. The photocurable composite of claim 1, wherein the light-curable resin is configured to polymerize upon exposure to light with a wavelength from about 280 nm to about 700 nm.

12. The photocurable composite of claim 1, wherein the light-curable resin is configured to polymerize upon exposure to light with a wavelength from about 315 nm to about 400 nm.

13. A method comprising
    exposing a photocurable composite of claim 1 to a wavelength of light from about 280 nm to about 380 nm, about 380 nm to about 700 nm, or a combination thereof, to provide a hardened material.

14. The method of claim 13, wherein the method comprises exposing the photocurable composite to the wavelength of light for a duration of about 0.1 second to about 15 minutes.

15. A kit comprising
    a light-curable resin comprising about 50 vol % to about 99 vol % of an acrylate-functionalized oligomer, wherein the backbone of the oligomer comprises a polyurethane, a polyether, a polyester, or a combination of any two or more thereof;

about 1 vol % to about 50 vol % of a radical-reactive diluent;

about 0.05 vol % to about 2 vol % of a photoinitiator; and about 0.05 vol % to about 25 vol % of a surface cure protection agent; and instructions for generating a photocurable composite of claim 1.

16. The kit of claim 15, wherein the kit further comprises a filler material.

17. The kit of claim 15, wherein the kit further comprises a filler material separate from the light-curable resin.

18. The kit of claim 15, wherein the instructions direct including about 20 wt. % to about 60 wt. % light-curable resin based on total weight of the composite.

19. A method of immobilizing a fracture of a subject, the method comprising molding a photocurable composite of claim 1 around an extremity of a subject to provide a molded composite; and exposing the molded composite to a wavelength of light from about 280 nm to about 700 nm to provide a hardened material.

\* \* \* \* \*